United States Patent [19]
O'Connor

[11] Patent Number: 5,895,430
[45] Date of Patent: Apr. 20, 1999

[54] PROSTHESIS FOR LONG FEMUR AND KNEE DISARTICULATION AMPUTATION

[76] Inventor: Roderick S. O'Connor, 6405 Via Arboles, Anaheim, Calif. 92807

[21] Appl. No.: 09/019,655

[22] Filed: Feb. 6, 1998

[51] Int. Cl.$^6$ .................................................. A61F 2/64
[52] U.S. Cl. ........................................ 623/39; 623/43
[58] Field of Search ............................ 623/39, 43, 44

[56] References Cited

U.S. PATENT DOCUMENTS

| | | |
|---|---|---|
| 168,140 | 9/1875 | Collins et al. . |
| 453,285 | 6/1891 | Kneider . |
| 489,258 | 1/1893 | Marks . |
| 492,583 | 2/1893 | Duffie . |
| 909,859 | 1/1909 | Apgar . |
| 1,216,367 | 2/1917 | Rowley . |
| 1,314,136 | 8/1919 | Gaines et al. . |
| 1,370,299 | 3/1921 | Flanagan . |
| 2,671,224 | 3/1954 | Regnell ............................ 623/44 |
| 4,312,081 | 1/1982 | Munny ............................ 623/39 |
| 5,139,526 | 8/1992 | Skardoutos et al. . |
| 5,171,325 | 12/1992 | Aulie ............................... 623/43 |
| 5,226,918 | 7/1993 | Silagy et al. . |
| 5,267,950 | 12/1993 | Weddendorf ..................... 623/43 |
| 5,746,774 | 5/1998 | Krammer ........................ 623/39 |

FOREIGN PATENT DOCUMENTS 599365 of 0000 Italy .

Primary Examiner—David H. Willse
Assistant Examiner—Suzette J. Jackson
Attorney, Agent, or Firm—Harold L. Jackson

[57] ABSTRACT

A prosthesis for leg amputation at the knee joint or short distance above the knee is disclosed which includes an upper leg socket and artificial lower limb pivotally coupled together by a knee bracket attached to upper leg socket. The knee bracket is also pivotally coupled to a hydraulic unit carried by the lower limb. The knee bracket provides a hinge arrangement for the knee joint above the end of the amputee's leg stump by several inches thus providing a more natural looking and operating artificial limb.

16 Claims, 4 Drawing Sheets

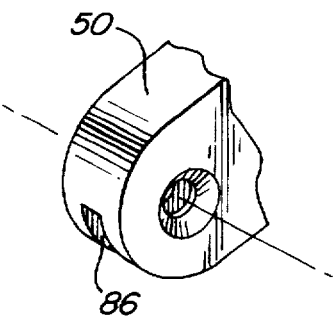
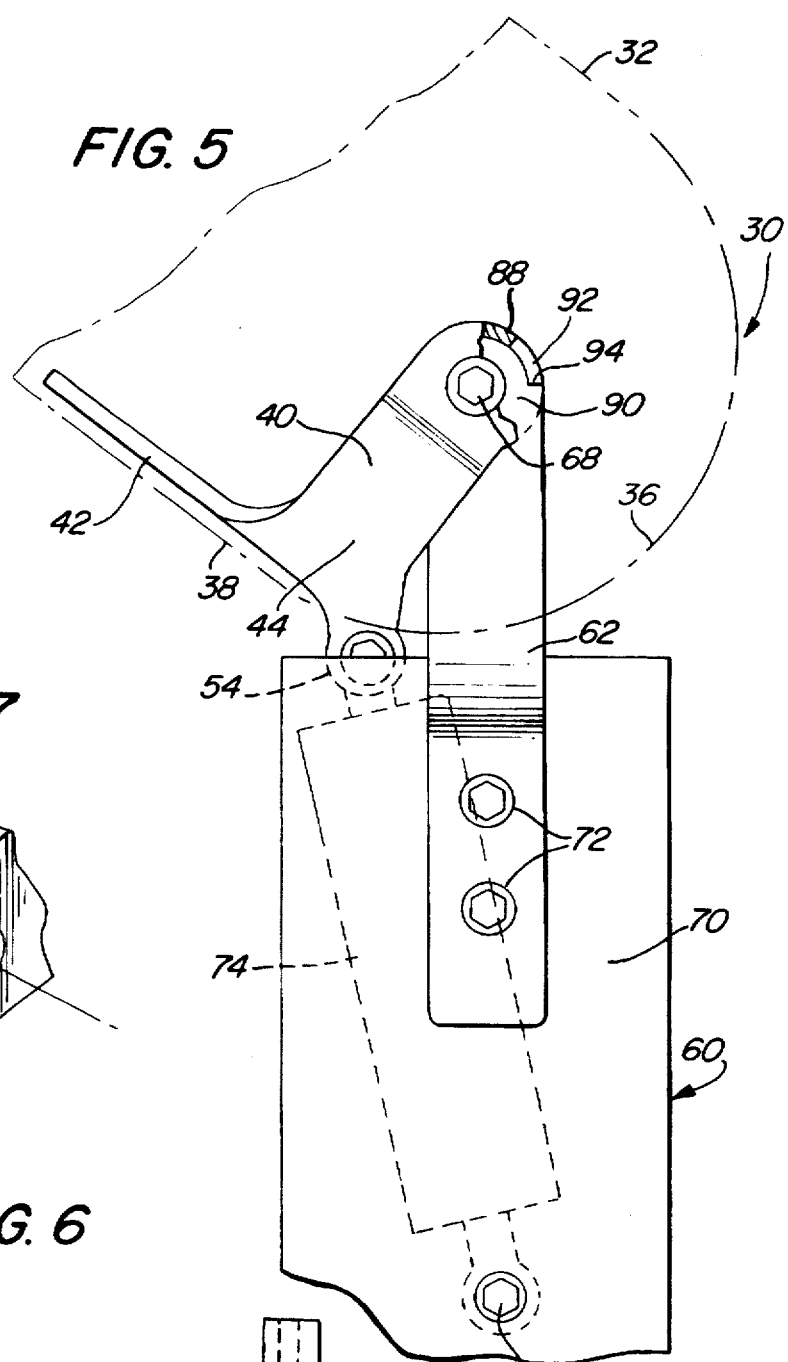
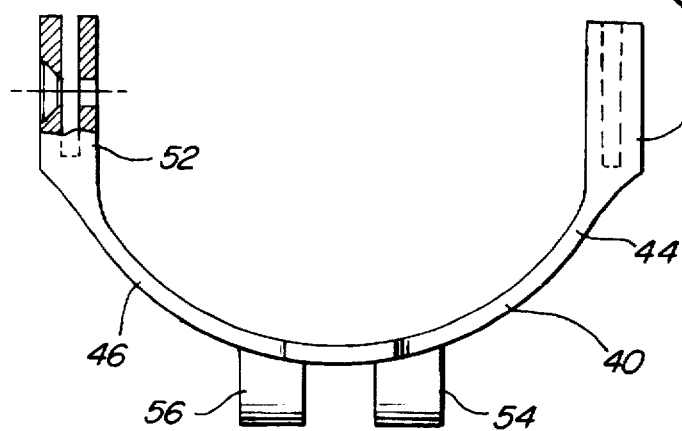

PROSTHESIS FOR LONG FEMUR AND KNEE DISARTICULATION AMPUTATION

FIELD OF THE INVENTION

This invention relates generally to prosthesis devices and, more particularly, it is directed to an improved long above the knee and knee disartic prosthesis.

BACKGROUND OF THE INVENTION

Generally, the art of prosthesis is old and many attempts have been made to achieve endoskeleton prosthesis which restores function and is also provides cosmetically aesthetic appearance. Artificial limbs that reproduce natural movement are desired so the user can function normally in society performing typical daily tasks and routines at both work and home. In the United States attempts to make acceptable prosthetic devices date back to the 1800's as illustrated in U.S. Pat. No. 168,140 "Artificial Leg" to Collins and McCalla (1875); No. 489,258 "Artificial Limb" to Marks (1893); No. 453,285 "Artificial Leg" to Kneider (1891); No. 492,583 "Artificial Leg Attachment" to Duffie (1893); No. 909,859 "Artificial Leg" to Apgar (1909); No. 1,216,367 "Artificial Leg" to Rowley (1917); No. 1,314,136 "Artificial Leg" to Gaines and Erb (1919); No. 1,370,299 "Artificial Limb" to Flanagan (1921); No. 5,139,526 "Long Above Elbow and Elbow Disartic Prosthesis" to Skardoutos et. al (1992), and No. 5,226,918 "Prosthesis with Adjustable Fitting Clearance" to Silagy and Lenze (1993). As people with disabilities are becoming increasingly active in today's society, continued efforts are being made to develop more functional artificial limbs.

For leg amputations, prior art prosthesis devices have mainly been designed for amputations which occur below the knee as exemplified in a number of the above listed US Patents. Since the knee joint is left in tack, it still has functionality and the prosthesis merely replaces the lower leg portion typically with an artificial leg shin and foot. While factors such as weight and leg attachment must still be addressed to create a natural working lower leg, the knee joint is still used to provide the pivotal point for the lower leg and simplifies the prosthesis design. However, for the most part prior art including the aforementioned prior art patents do not provide an adequate prosthesis solution for the particular problems that arise for amputation at or just above the knee. Such amputations either disable the knee joint or take it out altogether, and therefore a properly functional prosthesis device must include a suitable arrangement that substitutes for the former knee.

A conventional prosthesis to accommodate a leg stump of an amputee which attempts to incorporate a knee joint arrangement is illustrated in FIGS. 1 and 2, which prosthesis includes an upper leg socket section 20 for receiving a leg stump and a lower leg section 22. The upper leg socket section is attached to the lower leg section by knee joint 24. The knee joint 24 rotates or swings about the knee axis 26 which is established in the knee joint 24 by knee axis bolt 28 which pivotally couples the upper and lower leg sections. As the knee joint 24 is connected near the bottom of the upper leg socket section 20, the knee axis 26 may end up as much as about 2½ to 3½ inches below the bottom of the leg stump. Additionally, since the knee joint side attachments depend on a single axis bolt to create the knee joint pivot, a properly aligned knee axis pivot is difficult to achieve.

While most prior art leg prosthetic arrangements, such as the examples listed above, are fine for short or mid-length femur amputations, these arrangement typically result in several functional and cosmetic problems for long femur and knee disarticulation amputations. Functionally, it results in an awkward stride length, stride timing, and gait pattern for the amputee, and thus a natural appearing walk is not possible. Cosmetically, this arrangement results in a longer than desired leg thigh section and corresponding short shin section. This looks unpleasant while the amputee is in a sitting position, as the prosthetic knee sticks out further that the sound knee and the short shin section may leave the foot swinging in the air when it does not reach the ground. Furthermore, while walking the shin section has less weight and shorter pendulum swing, resulting in an undesirable swing period which does not match the sound side leg. Patients do not desire a prosthesis with these shortcomings and an improved leg prosthesis without the foregoing disadvantages would provide a desirable advancement in the prosthesis art. It should be noted that a knee disarticulation amputation, if possible, provides a much more solid support for a prothesis than an amputation of the femur. Amputation of the femur leaves only a small diameter of bone end for support as contrasted to the relatively large bone mass at the knee joint.

SUMMARY OF THE INVENTION

It is therefore an object of this invention to provide a prosthesis that allows placement of the knee joint pivot to be more favorably positioned.

Another object of the invention is to provide a prosthesis structure with few parts that is simple and easy to make and fit to a user.

A further object of the invention is provide leg prosthesis that provides a natural appearance and movement.

Features of the invention useful in accomplishing the above objects to achieve a prosthesis in relation to amputations just above or at the knee joint area include a leg prosthesis with a knee hinge arrangement located a preselected distance above the bottom of an upper leg socket member that receives the leg stump. A knee bracket affixed to the upper leg socket member is pivotally attached to a lower leg portion with the pivot point established above the bottom of the upper leg socket member. The knee bracket is also attached to a hydraulic unit which is housed in and attached to the lower leg portion. This arrangement creates an artificial knee joint above the bottom of the upper leg socket member providing a more natural looking and operating artificial limb.

Additional features of the invention may include a single knee bracket that provides all pivotal attachments between the upper leg socket member and lower leg portion of the leg prosthesis. More specifically, the knee bracket has two arms which extend in a U-shaped fashion around both sides of the upper leg socket member. These arms of the knee bracket provide the means to pivotally attaching the upper leg socket member to the lower leg member, and also to pivotally attach the hydraulic unit to the lower leg portion. The knee bracket simplifies the knee pivotal structure while providing a reliable joint mechanism for the prosthesis. The construction and operation of preferred embodiments of a prosthesis device of the present invention may best be understood by reference to the following description taken in conjunction with the accompanying drawings.

3

Figure 1:
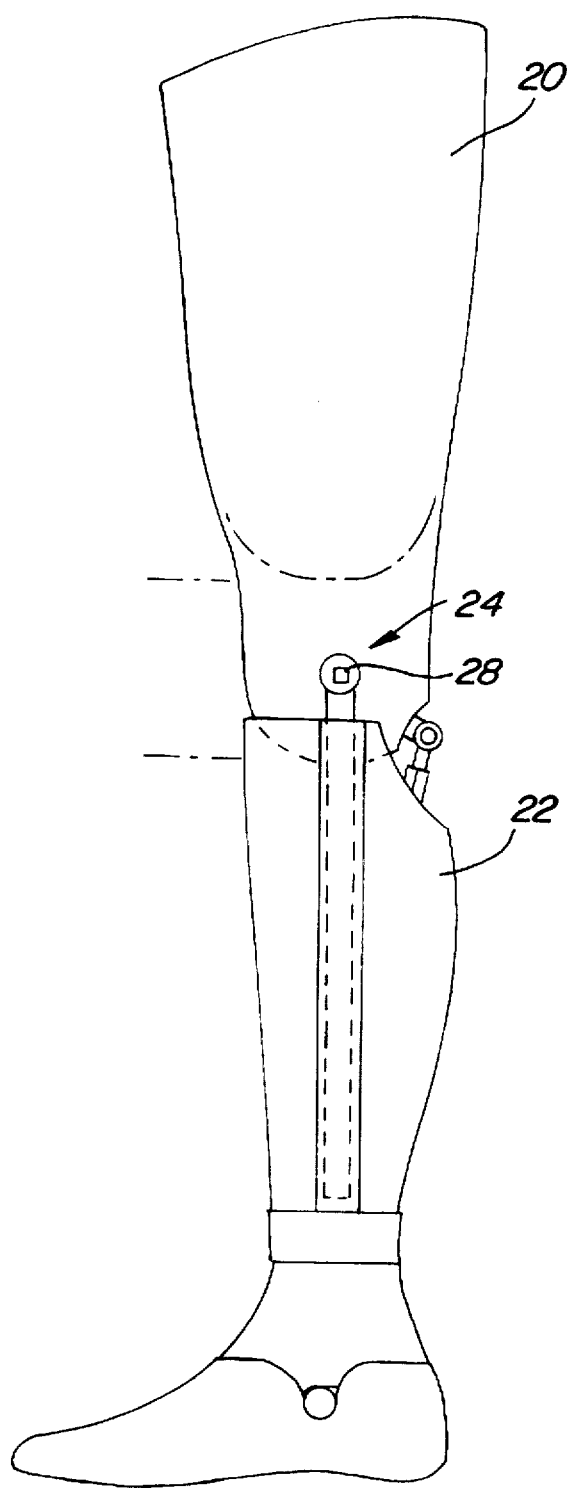
FIG. 1 is a side elevational view of a prior art prosthesis in accordance with the principles of the invention.
Figure 2:
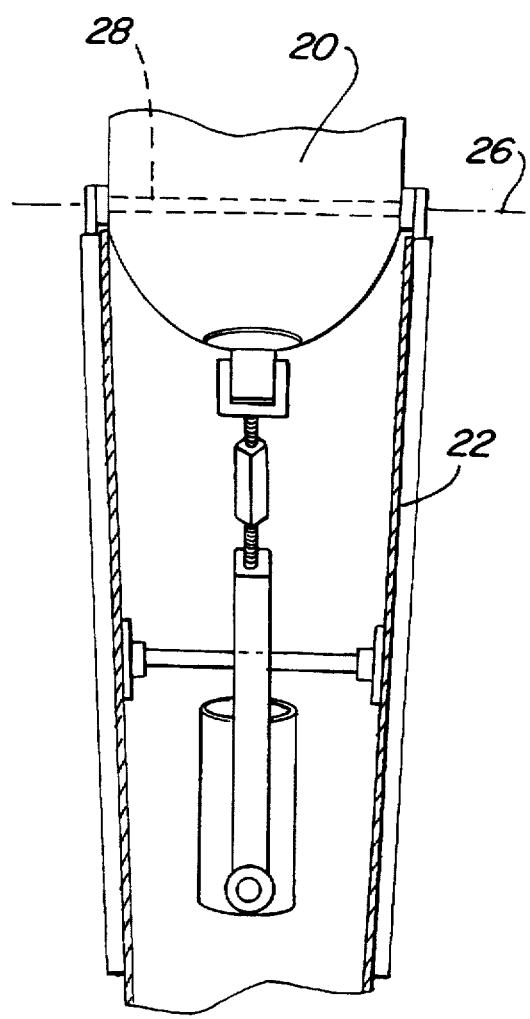
FIG. 2 is a partial cross-sectional rear view of the prior art prosthesis in FIG. 1.
Figure 3:
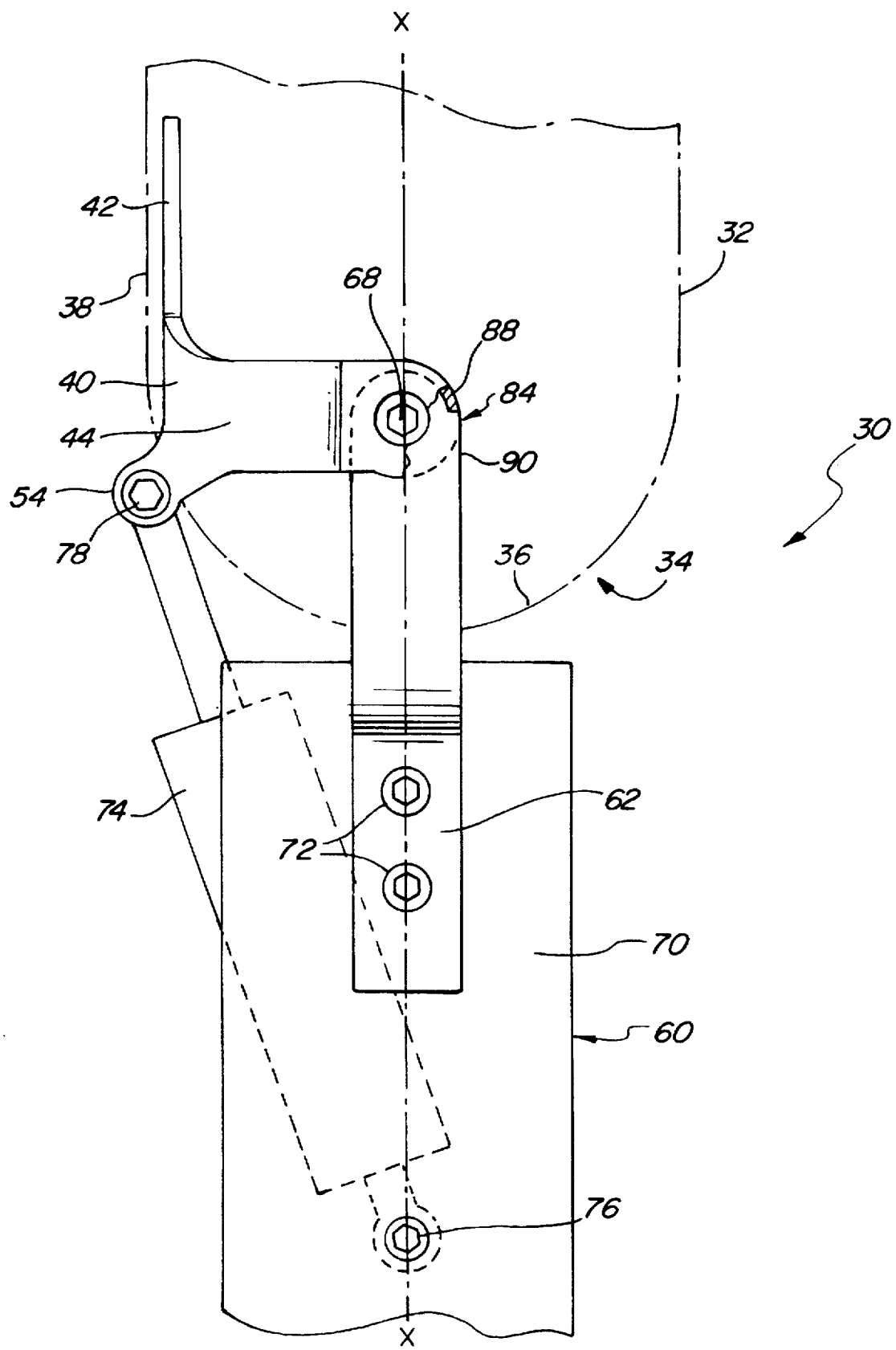
Figure 4:
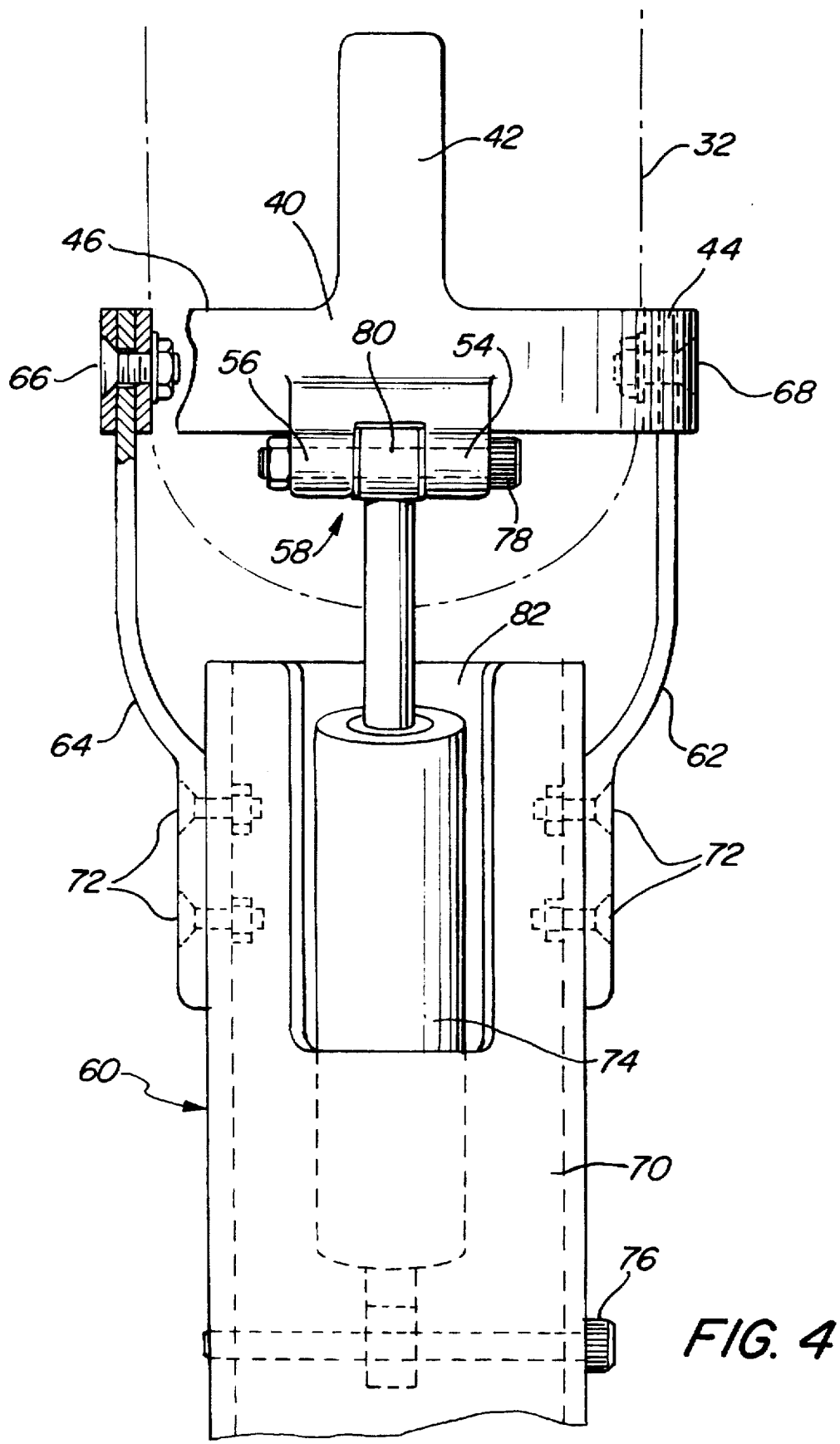

FIG. 3 is a side view of the leg prosthesis in accordance with the principles of the invention;

FIG. 4 is a rear view of the knee bracket and upper leg socket member (shown in phantom) attached to the lower leg portion of the leg prosthesis;

FIG. 5 is a side view of the leg prosthesis in the flexed, bent leg position;

FIG. 6 is a top view of the knee bracket shown partially in section, and

FIG. 7 is a partially perspective view of the clevis portion of the knee bracket showing its stop mechanism.

DESCRIPTION OF THE PREFERRED EMBODIMENT

Referring now to the drawings and more particularity to FIG. 3, there is shown a preferred prosthesis 30 including a limb socket or upper leg attaching member 32 (shown in phantom) shaped and sized for receiving the leg stump of an amputee (not shown). The socket member 32 accordingly has an open end at the top portion and a closed end 34 forming a bottom area 36 and a longitudinal axis x—x. The socket member 32 is typically made of a plastic material well known in the art. A knee bracket 40 is attached to the lateral back wall portion 38 of the socket member 32. The knee bracket 40 includes a tongue portion 42, which in this embodiment extends upwardly along the lateral wall portion 38 of the socket member 32 preferably being affixed thereto by laminating the tongue portion 42 into the lateral wall portion 38. The knee bracket 40 extends in a U-shaped fashion into two arms 44 and 46 each arm terminating into two clevis 50 and 52, shown more clearly in FIG. 6. When the knee bracket is attached to the back wall of the socket member, the arms 44, 46 extend forwardly about half the way around the socket member, such that clevis 50, 52 may be aligned closely with the pivotal axis of the leg stump former knee. Additionally, the knee bracket 40 has another attachment arrangement on its lower rear portion, generally designated by reference number 58, which in this embodiment comprises two spaced apart colinearly sleeves 54 and 56 disposed horizontally on its lower rear portion.

The lower leg portion, generally designated by reference number 60, has two upwardly extending lower joint brackets 62 and 64. The upper end portions of the lower joint brackets slide into clevis 50 and 52 respectively as shown more clearly in FIG. 4. These brackets are pivotally coupled to the knee bracket clevis portion by means of screws 66 and 68, with the lower joint bracket freely pivoting on the screws. By this bracket arrangement the pivot axis between the socket member 32 and lower leg portion 60 can be established above the bottom area or wall 36 of the socket member by a preselected distance such as, for example, one inch or more and preferably about 2 to 3½ inches.

Lower joint brackets 62 and 64 at the other ends are fixedly attached to the lower leg chassis 70 by means of screws and nuts 72. Lower leg chassis 70 houses hydraulic unit 74 which assists in proper lower leg movement when in use. The hydraulic unit 74 is pivotally mounted to the lower leg chassis 70 at one end thereof by means of lower bolt 76 which extends through the chassis. The other end of the hydraulic unit is pivotally coupled to the knee bracket 40 by means of upper bolt and nut 78 which extends through the sleeves 54 and 56 and the end portion 80 of the hydraulic unit placed therebetween. The opening 82 in the rear of the lower leg chassis provides for the back and forth motion of the hydraulic unit, as can be more clearly seen in FIG. 4.

Referring to FIG. 5, the knee bracket 40 and lower joint brackets 62 and 64 have a cooperative stop arrangement,

4 designated generally by reference number 84, for limiting the forward movement of the lower leg portion 60. The knee bracket clevis 50 and 52 each have a stop portion 86 on the periphery edge portion. This stop portion 86 on the clevis can more clearly be understood by referring to FIGS. 6 and 7. Essentially, peripheral edge of the clevis slot is partially closed by an arch shaped shoulder 88 which extends about half way around the radial portion of the clevis. On the pivotal end 90 of the lower joint bracket 62, 64 there is a radially disposed elongated notch 92 which extends around the radial portion of the end of the bracket terminating in stop 94. Accordingly when the pivotal end 90 of the lower joint bracket 62, 64 is slid into the clevis 50, 52 of the knee bracket (see FIG. 5), the arch shaped shoulder 88 pivots within the elongated notch 92 until the end of the shoulder or clevis stop 86, meets the lower joint bracket stop or notch stop 94. This arrangement provide a simple yet effective stop mechanism for the lower leg portion integrated into the knee bracket and lower joint brackets without any extra parts.

In operation, FIG. 3 shows the prosthesis in its straight position such as when the user is standing. The piston rod of the hydraulic unit 74 is extended and the stop 86 in the clevis joint of the knee bracket seats against the notch stop 94 of the lower bracket. Accordingly, the lower leg portion 60 is prevented from pivoting further forward and thus the knee joint will not bend backwards which would not look natural. In FIG. 5, the prosthesis is shown in its fully bent position with the piston in the hydraulic unit 74 fully compressed. From this bent position, the hydraulic unit assists the lower leg portion pivot forward in a more natural swing. In addition, the novel knee bracket and its pivot point can be positioned a preselected distance above the bottom of the leg socket member providing the lower leg portion with a longer swing arm which results in more natural overall gait for the user of the prosthesis device.

There has thus been described an improved prosthesis. The improved prosthesis device allows the prosthesis knee joint to be mounted above the end of the leg socket member in a more anatomically correct position. The knee bracket provides two independent side joint attachments, and therefore the side joint attachments can be more readily aligned to work together as one joint, mitigating knee alignment complications accompanied by conventional single bolt axis knee joint arrangements. Accordingly, various modifications of the prosthesis will occur to persons skilled in the art without involving any departure from the spirit and scope of the invention as set forth in the appended claims.

What is claimed is:

1. A prosthesis for accommodating an amputee's leg stump resulting from an amputation at or just above the knee joint, comprising:

an upper limb socket member having a back wall and a bottom wall, and adapted to be pivotally secured to a lower limb member, the bottom wall being arranged to receive the end of the amputee's leg stump;

a lower limb member;

a first bracket attached to the upper limb socket member;

a second bracket attached to the lower limb member and pivotally attached to the first bracket above the bottom wall whereby the axis about which the two members pivot is located above the bottom wall of the upper limb socket member; and a hydraulic unit having two ends, one end pivotally attached to the lower limb member and the other end attached to the first bracket above the bottom wall.

2. The prosthesis defined in claim 1 wherein the first and second brackets pivotal attach above the bottom wall by more than about 1 inch.

3. The prosthesis defined in claim 2, wherein the pivotal attachment occurs between about 2 and 4 inches above the bottom wall of the upper limb socket member.

4. The prosthesis defined in claim 2 wherein the first bracket and hydraulic unit pivotally attach above the bottom wall by more than about 2 inches.

5. The prosthesis defined in claim 2 wherein the the hydraulic unit and the second bracket are pivotally attached to the first bracket at about the same distance above the bottom wall of the upper limb socket member.

6. The prosthesis defined in claim 1 wherein the first bracket is laminated into the back wall of the upper limb socket member.

7. The prosthesis defined in claim 1 wherein the first bracket and second bracket further include means for limiting the forward movement of the lower limb member.

8. A prosthesis for accommodating an amputee's upper leg stump resulting from knee disarticulated or long above the knee amputation, comprising:

an upper leg attaching member defining a stump socket having a bottom wall being arranged to receive the end of the leg stump;

a lower limb member;

and hinge means for attaching the upper leg attaching member to the lower limb member to provide a pivot axis between said members above the bottom wall of the upper leg attaching member and the lower end of the amputee's leg stump wherein the hinge means comprises a knee bracket attached to the upper leg attaching member having two arms extending about one-half of the wave around the upper leg attaching member and a pair of joint brackets carried by the lower limb member with the upper ends thereof pivotally secured to the arms.

9. The prosthesis of claim 8 wherein the pivot axis is at least about one inch above the bottom wall of the upper leg attaching member.

10. The prosthesis of claim 9 wherein the pivot axis is between about two to three and one-half inches above the bottom wall of the upper leg attaching member.

11. The prosthesis of claim 8 further including a hydraulic member connected at one end to the lower limb member wherein the knee bracket has a sleeve and pin arrangement for pivotally mounting the other end of the hydraulic unit.

12. The prosthesis of claim 11 wherein the knee bracket includes an integral stop means for limiting forward movement of the lower limb member.

13. The prosthesis of claim 12 wherein the knee bracket is attached to the upper limb member by lamination.

14. The prosthesis of claim 13 wherein the knee bracket has two clevis joints for pivotally attaching the lower joint brackets.

15. The prosthesis of claim 14 wherein the knee bracket clevis joints and lower joint brackets each have integral stops for limiting the forward movement of the lower limb chassis.

16. A prosthesis for use by an amputee with a remaining upper leg stump extending to about the natural knee joint, comprising:

a cone shaped socket member having a top open end for receiving the stump and a closed bottom wall being arranged to support the stump end, and further having a longitudinal axis;

a knee bracket carried by the socket member and extending on opposite sides thereof;

a lower leg chassis; and two lower joint brackets secured at one end on opposite sides of the lower leg chassis and pivotally attached to the knee bracket at the other end, the pivotal attachment between the knee bracket and said other end of the lower joint brackets forming pivot points on opposite sides of the socket member along a pivot axis generally perpendicular to the longitudinal axis of the socket member and above the bottom wall thereof.

* * * * *

UNITED STATES PATENT AND TRADEMARK OFFICE
CERTIFICATE OF CORRECTION

PATENT NO. : 5,895,430
DATED : April 20, 1999
INVENTOR(S) : Roderick S. O'Connor It is certified that error appears in the above-indentified patent and that said Letters Patent is hereby corrected as shown below:

Column 5, line 31, delete "wave" and insert --way--.

Signed and Sealed this

Seventh Day of September, 1999

Attest:

Q. TODD DICKINSON

Attesting Officer

Acting Commissioner of Patents and Trademarks